(12) United States Patent
Haeffner et al.

(10) Patent No.: US 6,532,420 B1
(45) Date of Patent: Mar. 11, 2003

(54) PRODUCTION OF ANIMAL FEED

(75) Inventors: Jürgen Erwin Friedrich Haeffner, Saint-Could (FR); Guy Harari, Dunwoody, GA (US); Thomas D'Alfonso, Sceaux (FR)

(73) Assignee: Aventis Animal Nutrition S.A., Antony (FR)

( * ) Notice: Subject to any disclaimer, the term of this patent is extended or adjusted under 35 U.S.C. 154(b) by 0 days.

(21) Appl. No.: 09/653,549

(22) Filed: Aug. 31, 2000

Related U.S. Application Data

(60) Provisional application No. 60/151,760, filed on Aug. 31, 1999.

(30) Foreign Application Priority Data

Apr. 14, 2000 (EP) .............................. 00108350

(51) Int. Cl.$^7$ ............................ G01N 31/00; G06F 19/00
(52) U.S. Cl. ............................................. 702/22; 426/531
(58) Field of Search ........................ 702/27, 22, 179; 426/2, 53, 54, 623, 630, 656, 531

(56) References Cited

U.S. PATENT DOCUMENTS

| | | | | |
|---|---|---|---|---|
| 4,117,170 A | * | 9/1978 | Washam | 426/72 |
| 4,211,796 A | * | 7/1980 | Lanter et al. | 426/2 |
| 4,225,621 A | * | 9/1980 | Lanter et al. | 426/2 |
| 4,234,604 A | * | 11/1980 | Betx et al. | 426/2 |
| 4,311,713 A | * | 1/1982 | Betz et al. | 426/2 |
| 4,401,680 A | * | 8/1983 | Young | 426/53 |
| 4,786,182 A | * | 11/1988 | Larsen | 366/140 |
| 5,720,971 A | * | 2/1998 | Beauchemin et al. | 424/438 |
| 5,922,343 A | * | 7/1999 | Stucker | 424/438 |
| 5,952,193 A | * | 9/1999 | Shimamura et al. | 435/68.1 |
| 6,070,128 A | * | 5/2000 | Descales et al. | 702/30 |
| 6,076,043 A | * | 6/2000 | Liu | 702/2 |
| 6,166,382 A | * | 12/2000 | Baker et al. | 250/339.12 |
| 6,169,232 B1 | * | 1/2001 | Hey et al. | 800/320.1 |
| 6,238,709 B1 | * | 5/2001 | Kalmach | 426/2 |
| 6,248,939 B1 | * | 6/2001 | Leto et al. | 800/320.1 |
| 6,333,062 B1 | * | 12/2001 | Fontana et al. | 426/635 |

FOREIGN PATENT DOCUMENTS

| | | |
|---|---|---|
| WO | WO 83/02158 | 6/1983 |
| WO | WO 89/11090 | 11/1989 |

OTHER PUBLICATIONS

Van Kempen et al., "NIRS Mav Provide Rapid Evaluation of Amino Acids", Feedstuffs, Dec. 2, 1996.
Van Kempen et al., "Near–Infrared Reflectance Spectroscopy in Precision Feed Formulation", J. Appl. Poultry Res. 6: 471–477 (1997).
Copy of co–pending application No. 09/918,512, filed on Aug. 1, 2001.
Amino News, " Amino acid variation in compound feed: Practical relevance and means to control variability", vol. 1, No. 3, Dec. 2000.
Copy of co–pending application No. 09/918,483, filed on Aug. 1, 2001.

* cited by examiner

*Primary Examiner*—John S. Hilten
*Assistant Examiner*—Demetrius Pretlow
(74) *Attorney, Agent, or Firm*—Finnegan, Henderson, Farabow, Garrett & Dunner, L.L.P.

(57) ABSTRACT

A method of selecting and enhancing of feedstuffs for use in an animal feed product by analyzing the statistical distribution of the nutritional content of batches of the feedstuff and calculating the number of batches within a predetermined range of a desirable nutrient composition. The cost of enhancing the feedstuff by adding nutrient additives is calculated and batches of the feedstuff are accepted or rejected, with the enhancement step only applied to the accepted batches. The method can be applied to products such as soyabean meal and corn which are major constituents of animal feed. It produces a feedstuff with a lower than natural variance in nutrient composition and a guarantee of a desired nutritional composition without the need for systematic overformulation of the product.

15 Claims, 5 Drawing Sheets

PRODUCTION OF ANIMAL FEED

This application claims benefit under 35 U.S.C. §119(e) to U.S. provisional application No. 60/151,760, filed on Aug. 31, 1999. This application also claims benefit under 35 U.S.C. §119 to European patent application no. 00 1083500, filed on Apr. 14, 2000. The contents of both priority documents are incorporated by reference herein.

The present invention relates to the production of animal feed and in particular to the selection and enhancement of raw materials for use in animal feed production.

Animal feeds typically consist of a mixture of materials. For instance, a typical composition for a feed for poultry is 25% soyabean meal, 50% corn, 20% byproducts suitable for animal feed and 5% minerals, vitamins, supplements and other feed additives. Feeds for other animals have different compositions, and soyabean meal is one of the most important vegetable protein sources for animal feeds in general. For instance, it is one of the main components of feed for poultry.

In order to achieve the most efficient growth of animals, the diet needs to be carefully controlled and thus the nutrient composition of the feedstuff is of high importance. However, natural raw materials have a high variation in nutrient composition. For instance, soyabean meal is generally classified into high and low protein products, namely high protein soyabean meal (HPSBM) with 49% protein and low protein soyabean meal (LPSBM) with 44% protein. High protein soyabean meal is of a higher price than low protein soyabean meal but in reality neither have a fixed level of protein, but vary within certain tolerance limits about the average value. The price of a raw materials such as soyabean meal is also variable; however, the prices among raw materials are often highly correlated because they may be a function of nutrient composition. In addition, soyabean meal also provides protein to the diet and the comprising amino acids and other nutrients. These other nutrients are very important in obtaining optimal performance of the feed, but the amount of the amino acids, respectively the first limiting amino acids: lysine, methionine, threonine and tryptophane, vary widely between different batches of soyabean meal. For example, the coefficient of variation (CV) of lysine and methionine composition amongst batches of soyabean meal can be approximately 10%.

In order to guarantee the level of desired nutrients in the feed, it has been proposed to measure the level of nutrient in raw material for the feed, and to supplement that level where necessary with additional components, such as synthetic nutrients. For instance, synthetic methionine can be added to the diets containing soyabean meal. In the case of the amino acid levels in soyabean meal, these can be assessed by inspecting the near infrared spectrum of the soyabean meal. It has been found that the near infrared spectrum (NIRS) of soyabean meal is dependent upon the amino acid content. By establishing a database relating the NIR spectrum to the amino acid levels (measured by other means), it is possible to use the NIR spectrum of a given batch of soyabean meal to assess its amino acid content.

Such techniques are described in "Near-Infrared Reflectance Spectroscopy in Precision Feed Formulation" by Van Kempen and Simmins; Applied Poultry Science, 1997, pp 471–475 and "NIRS May Provide Rapid Evaluation of Amino Acids" by Van Kempen and Jackson, Feedstuffs, Dec. 2, 1996.

The known method may be applied to any of a number of feedstuffs and their comprising nutrients. For example, the caloric content, and specifically the metabolizable energy content of corn or the fat composition of bakery by-product meal, or the amino acid and caloric content of animal by-products, are examples to which the method applies.

A more typical way of providing a guaranteed level of nutrient is to assess the natural variation of the level of nutrient in the raw material and to add a sufficient amount of supplement to all batches of the raw material to achieve a guaranteed high level. Clearly this techniques does not reduce the natural variation in level, but raises the average level to the high level. However the content of nutrient in the diet containing this raw material may still be overestimated, the requirements of the animals are not met and the performance is reduced. To minimise this risk safety margins are used for the formulation of the feed. These safety margins result in a systematic overformulation of specific nutrient ingredients and such overformulation is costly and reduces efficiency.

During an analysis of the economic variability of soyabean meal and the variability of amino acids among batches of soyabean meal, an unexpected discovery was made. Whereas it was possible to guarantee a high level of a specific nutrient (e.g. methionine) among all of the batches by setting a high specification and supplementing (with synthetic methionine), the price of the enhanced raw material was limited vis-a-vis the price of comparable raw materials, especially soyabean meal products and other protein-providing raw materials. In fact, if a feedmill had NIR and supplemental methionine, the enhanced product by this method provided no economic advantage. However, it was discovered that certain clusters of soyabean meal could be identified farther up the supply chain (e.g. at a soy crusher) that had certain nutritional profiles that made these batches consistently favorable to feed formulation software that chooses the optimal raw materials to have in inventory and to be included in the feed formulations at that mill. These clusters were systematically undervalued if one looked only at the expected profile of nutrient composition rather than the measured values, in this case with NIRS, and the relative proportions of nutrients with respect to the specifications among all of the feed formulas produced by the feedmill. Furthermore, a threshold value could be determined for which minimal supplementation of the desired nutrients was necessary, for which enough product could be manufactured to meet anticipated demand for this product, and for which the guaranteed nutrient profile was higher in value than the price of supplement and raw material. In this example, total methionine and lysine, digestible methionine and lysine, and total protein could be measured in batches of soyabean meal with NIRS, clusters were discovered which had relative proportions of these nutrients close to a predetermined threshold value, minimal supplementation of only synthetic methionine were needed, and diets formulated with this enhanced product were lower in cost, lower in variability, and higher in digestibility than that which could be obtained by conventional feed formulation with existing raw materials.

SUMMARY OF THE INVENTION

The present invention provides a method of analyzing, selecting and enhancing raw materials for use in animal feed products in a manner which eliminates the systematic overformulation, while guaranteeing a desired level of nutrient in the supplemented product. The invention also provides a method of determining a threshold value while considering the objectives of economic as well as nutritional value.

In more detail, according to one aspect, the present invention provides a method comprising the steps of:

analyzing the nutritional composition of batches of a raw material for use in an animal feed product;

comparing the nutritional composition with a predetermined nutritional composition;

calculating the amount of supplemental nutrient needed to bring the composition of the batch to the predetermined nutritional composition;

determining a threshold value for which clusters of the raw material exist that are both economically and nutritionally favorable;

screening the batches to reject those for which the amount of supplemental nutrient needed is greater than a threshold value and to accept those for which the amount of supplemental nutrient needed is less than a threshold value; and supplementing only the accepted batches of raw material with the calculated amount of supplemental nutrient.

The method can further include a step of analyzing the statistical distribution (i.e. frequency) of the nutritional content of batches of the raw material, assessing the number of batches for which the amount of supplemental nutrient needed is less than the threshold value, and performing the screening and supplemental step on condition that the number of batches is greater than the predetermined value. This may conveniently be done by setting a nutritional composition threshold and comparing the nutritional content of each batch with the threshold, and rejecting those falling below the threshold.

The nutritional composition threshold may define the boundary of a range of nutritional compositions near to a predefined nutritional composition profile and the step of analyzing the statistical distribution of the nutritional content of the batches of the raw material may comprise estimating the percentage of batches that are clustered within that range.

DETAILED DESCRIPTION OF THE INVENTION

In the method of the present invention, the nutritional composition can be the amount of at least one amino acid such as methionine or lysine in the raw material. This can be measured by a fast, convenient, "in vitro" analysis technique such as near infrared reflectance spectroscopy (NIRS). In this case, a database can be established relating the NIRS spectrum of the raw material to the amino acid content and subjecting incoming batches to spectroscopy, then using the database to derive the amino acid content.

In the method of the present invention, the digestibility of the nutrient in the raw material can also be measured. This is measured in the same way for the amount of amino acid, namely analysis using NIRS. Again, a data base is established as above. For the purposes of the present invention, digestibility is defined as the proportion of a particular nutrient that is actually available to the animal to metabolize, for example "available phosphorus" refers to the amount of phosphorous that is metabolized by the animal; digestible amino acids are the amount of amino acids metabolized by the animal and metabolizible energy is the amount of calories in the feed that is actually metabolized by the animal.

Alternatively, the nutritional composition can be the amount of fat or oil in the raw material, the caloric content, the mineral content such as calcium and phosphorus, the available, digestible, or metabolizable portion of these or other nutrients.

The method is particularly suitable for application to raw materials, such as soyabean meal and corn, or byproducts such as animal byproducts, which are major components in animal feed.

The invention can be performed by an analysis and enhancement system that includes an analysis device (which may be an NIRS device), a data processing device, such as a programmed computer that executes the comparison and calculation steps, and a nutrient supplement supply device for supplementing the accepted batches of raw material. Thus, the invention encompasses a computer program adapted to control and execute the method on such a system.

The result of applying the invention is the production of an enhanced raw material with a consistent, desired level of nutritional value, and with a lower than natural variance in the nutritional value. This may result in lower pollution in form of nitrogen or phosphorus in the manure of animals fed diets containing the enhanced raw material.

The invention will be further described by way of example with reference to the accompanying drawings.

Figure 1:
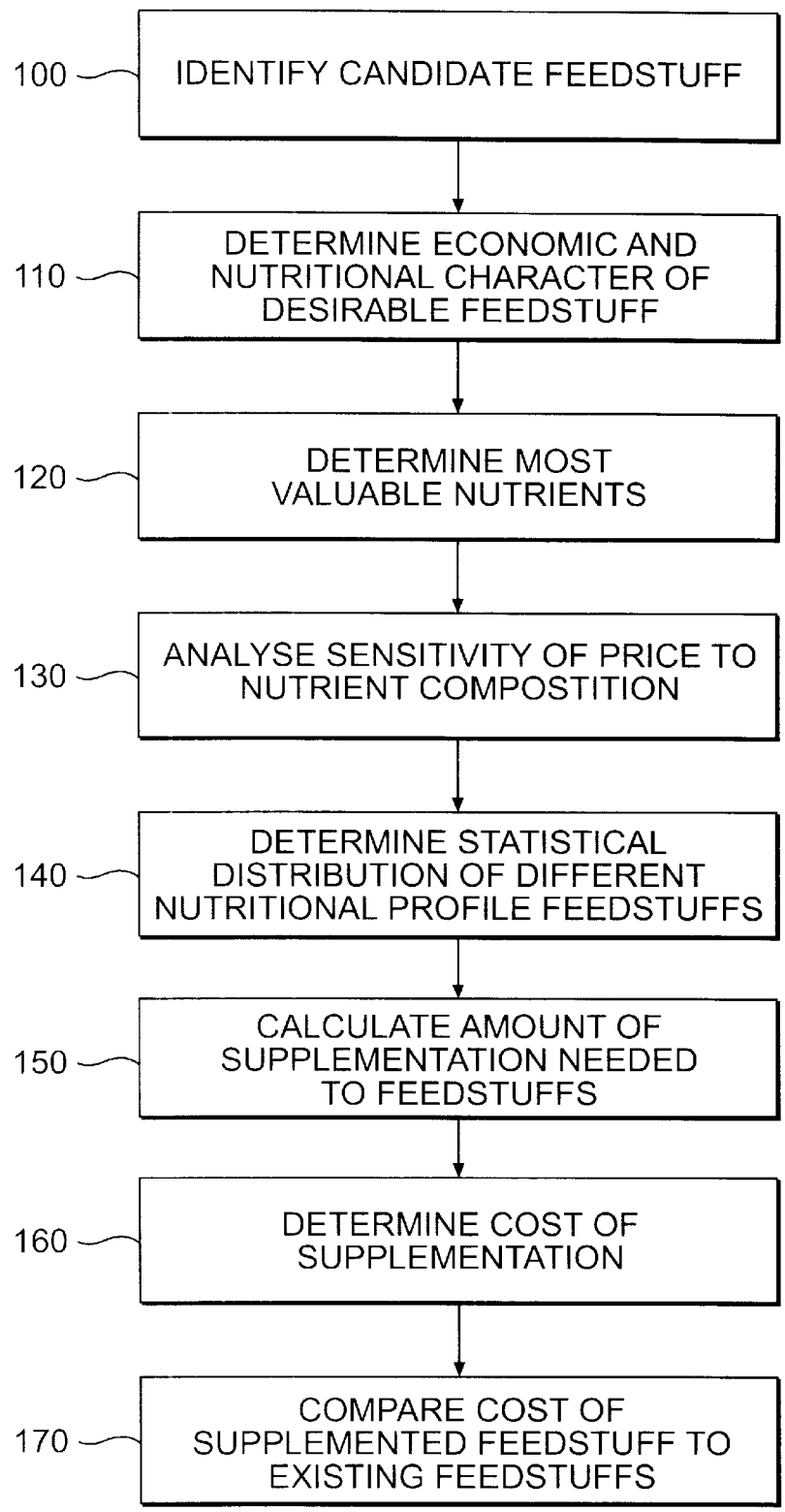
FIG. 1 is a flow diagram showing the overall decision making flow in an embodiment of the invention.

FIG. 1 illustrates the overall decision flow of an embodiment of the invention, and this will be described below while making reference to a particular application of the invention to the processing of soyabean meal, which, as discussed above, is one of the major constituents of animal feed.

Figure 2:
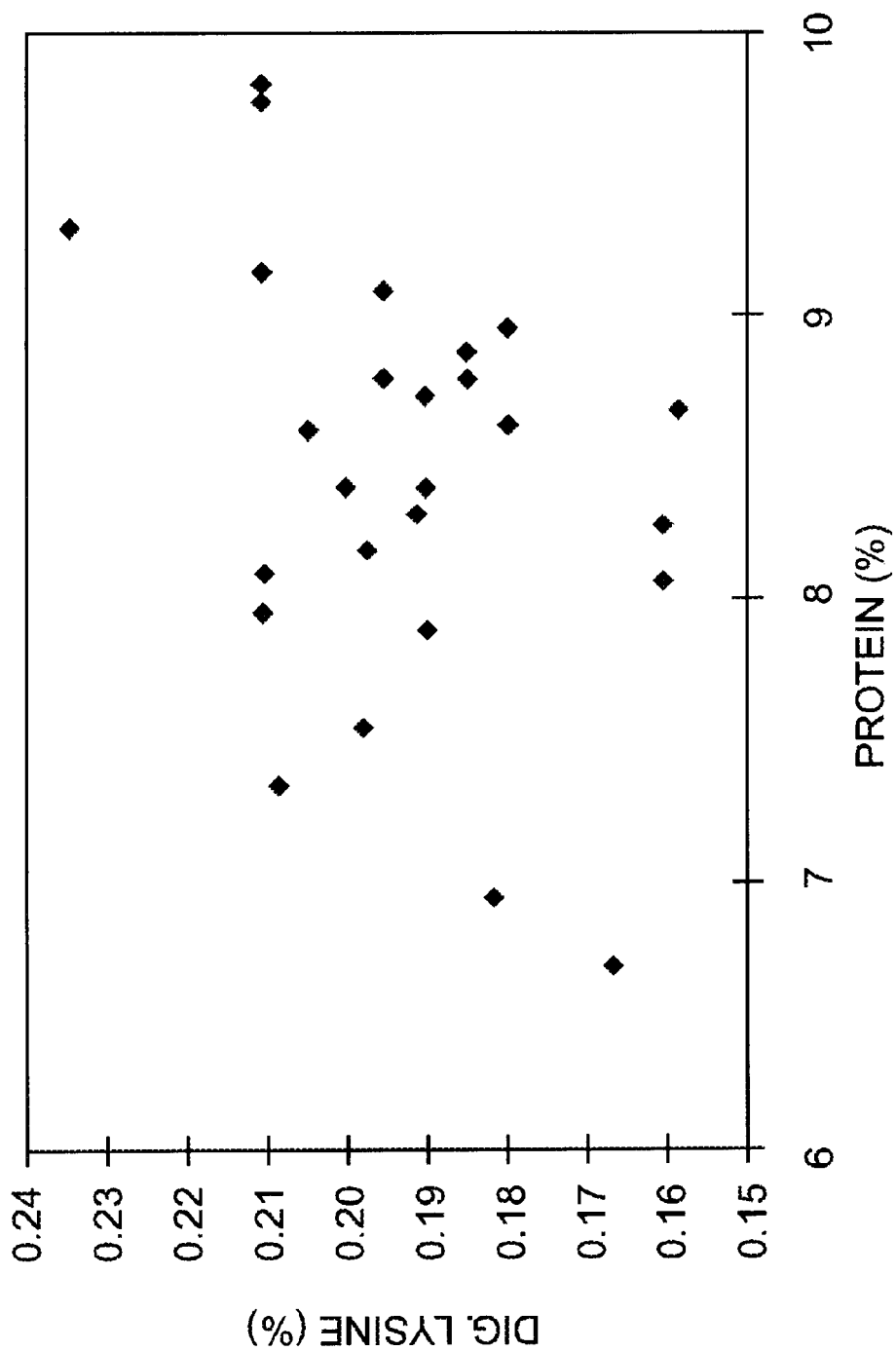
FIG. 2 is a graph illustrating the relationship between digestible lysine content and protein content in maize.

Referring to FIG. 1, in general terms the first step in the process is to identify a candidate feedstuff. Typically examples are soyabean meal, corn, or byproducts, such as bakery by-products, distillers by-products, or animal by-products. These feedstuffs can provide protein and other nutrients, such as amino acids, to the animal. However, the feedstuffs do not have a consistent content. FIG. 2 illustrates, in the case of corn, the variability in digestible lysine content as a function of the protein content of randomly selected batches. It can be seen that even if one were to select a consistent protein content, the digestible lysine content would vary markedly.

Therefore, in one aspect of the invention, the next step 110 determines the nutritional characteristics and economic characteristics (primarily acceptable price) of a desirable or ideal feedstuff. In the case of soyabean meal being used for poultry feed, as mentioned above, the soyabean meal is available basically as a high protein product (49%) or a low protein product (44%). The high protein product is more expensive at $160 per ton than the low protein product at $150 per ton. While the high protein product may be expected to have high levels of amino acid, in fact, it is found that there is a high variability in the amino acid level in both types of soyabean meal. Thus, even use of the high protein product cannot guarantee that the final feedstuff is of optimal value to the animal. Further, there is a difficult balance to be struck between the use of lower quantities of the more expensive high protein meal, or higher quantities of the lower protein cheaper soyabean meal.

According to an aspect of the invention, therefore, in step 120 the most valuable nutrients in the feedstuff are identified. In the case of soyabean meal, these are methionine and lysine. It is important to understand that not all of the nutrient present may be digestible to the animal. Thus, the total composition and the digestibility of the nutrients need to be considered. In this example, in the case of soyabean meal, it is desirable to have a digestibility of approximately 90%, as determined by NIRS screening.

Then, in step 130, the sensitivity of the feedstuff price to the nutrient composition is analysed. In the case of soyabean meal, it is desirable to have the methionine and lysine content identical, if possible, with high protein soyabean meal.

In step 140, it is then considered whether there is sufficient feedstuff available that can be economically enhanced with supplemental nutrient to satisfy the desired nutritional profile and thus a statistical analysis of the feedstuff is made. In the case of soyabean meal, it is found that the nutrient composition, particularly in terms of amino acid content is not uniformly distributed. Instead, the batches cluster in terms of their amino acid content. With an aspect of the invention, clusters are identified of batches of low protein soyabean meal that, despite being low in protein, are high in both total and digestible composition of amino acid. These batches require only a small amount of supplementation to achieve the desired nutritional profile, namely an amino acid profile identical to that of high protein soyabean meal.

With regard to the statistical distribution of the feedstuff, the amount of supplementation needed for each of the batches in the selected clusters is calculated in step 150. This can be done by using a Monte Carlo simulation to determine the amount of supplementation needed on average and the distribution of that supplementation (minimum and maximum supplementation needed). In the case of soyabean meal, the clusters of low protein soya bean meal that are close to the high protein soyabean meal in terms of amino acid content are selected such that the minimum supplementation of methionine and lysine needed is 0% and the maximum 0.1%. In step 160, the cost of such supplementation, in terms of the raw material cost (for LPSBM this is $150 per ton), the cost of the supplement and the cost of the monitoring, analysis and supplementing equipment, is calculated.

Then, in step 170, the cost of producing the supplemented feedstuff is compared to the cost of existing competing feedstuff, such as HPSBM. Table 1 below illustrates the nutrient composition and economic value of soyabean meal in the case of LPSBM, HPSBM and the enhanced product, marked as guaranteed soyabean meal (GSBM). It can be seen that the price of LPSBM is $150 per ton, the price of HPSBM is $160 per ton and the price of GSBM at a selling price of $157.50 per ton still results in a reduced feed cost compared to the use of HPSBM. This is despite the fact that the cost of the additive needed is $1.60 per ton and the estimated cost of the equipment for screening the product and adding the additive is $0.75 per ton. It is therefore demonstrated that, using the procedure illustrated in FIG. 1, it is possible to select and enhance a raw material for a feedstuff in a manner that improves the nutritional value, while maintaining economic advantage for the user of the feedstuff. For example, batches of corn may be analyzed for caloric content. The amount of calories in corn that is digestible and metabolized by the animal is commonly referred to as "metabolizable energy" (ME). Following the invention described in FIG. 1, 1. Corn is identified as the feedstuff.
2. Clusters of corn batches with high ME and low cost can be discovered.
3. Sufficient batches of high ME corn exist for the market.
4. Threshold values of metabolizable energy composition are determined.
5. Supplemented energy in the form of vegetable oil may be used.
6. The net economic value of this new feedstuff can be calculated.

TABLE 1

Nutrient composition and economic value of soyabean meal with guaranteed composition

|  | LPSBM | HPSBM | GSBM | COMMENTS |
|---|---|---|---|---|
| Protein | 44% | 49% | 44% | same as Soy 44% |
| Lysine | 2,74% | 3,07% | 3,07% | same as Soy 49% |
| Methionine | 0,60% | 0,68% | 0,68% | same as Soy 49% |
| TSAA | 1,23% | 1,39% | 1,35% |  |
| Threonine | 1,72% | 1,94% | 1,83% |  |
| Metabolizable Energy | 2244 | 2420 | 2244 | same as Soy 44% |
| Other Nutrients | X | Y | X | same as Soy 44% |
| Meth 99 | 0% | 0% | 0,08% | Supplement needed |
| Raw Material Cost | 150,00 | 160,00 | 151,63 |  |
| Value | 150,00 | 160,00 | 157,50 | selling price |
| Net Value Added |  |  | $5.87 | per ton |
| Feed Price Difference | 145,75 | 145,50 | 145,00 −0,50 | reduced feed cost per ton |
| Nutrient Variance Difference | 4.56% | 4,25% | 3.40% −20% | reduced nutrient variation |

It is also worth noting that the variance in nutrient content is significantly reduced, even compared to the HPSBM. The variance in nutrient content of LPSBM is 4.56%, in the case of HPSBM it is 4.25%, but in the case of GSBM it is only 3.4%. Thus, the feedstuff manufacturer can use the enhanced produce without the need for monitoring the content or systematic overformulation, while still being confident of providing a feedstuff of guaranteed value to the animal.

Figure 3:
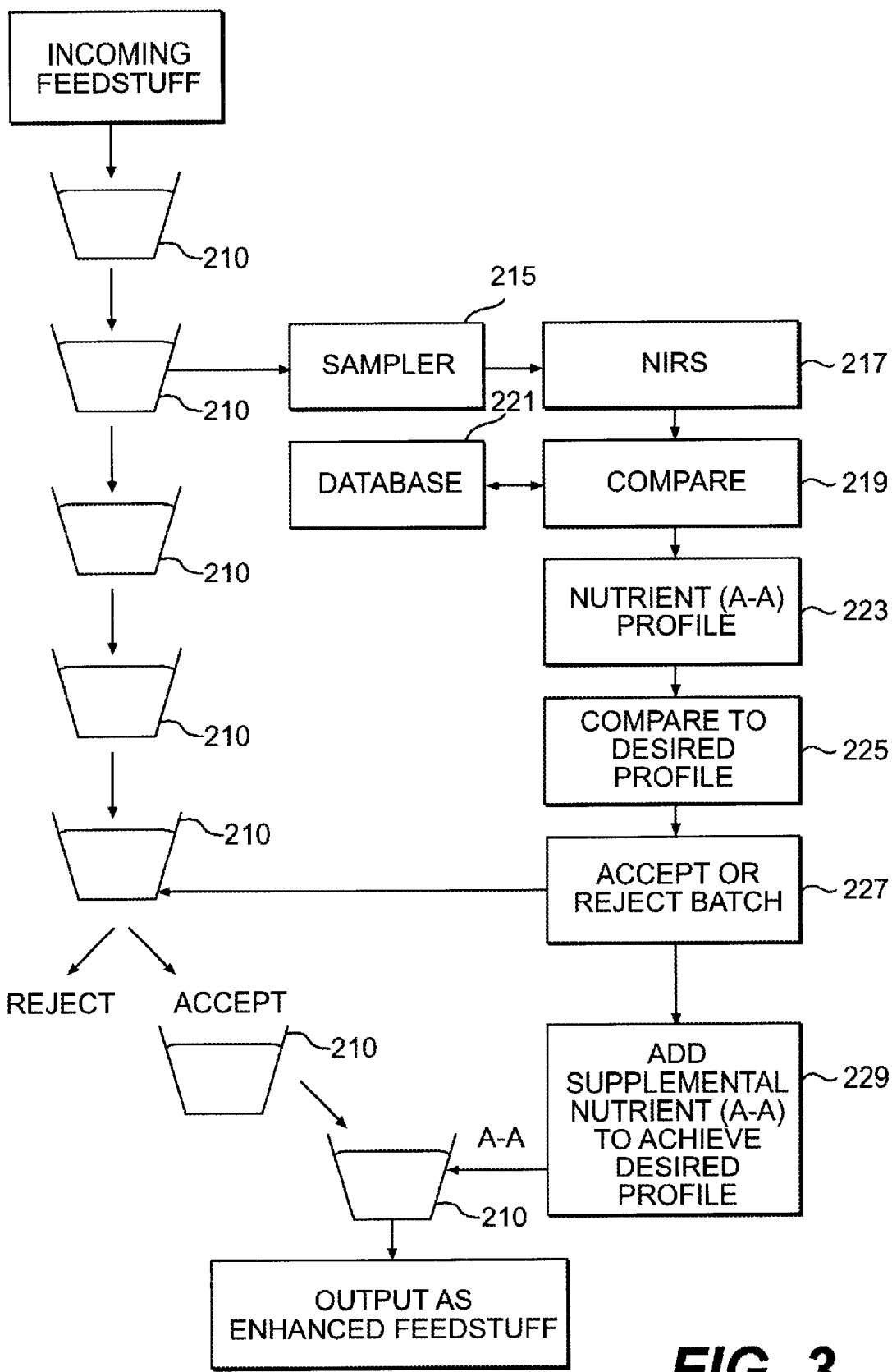
FIG. 3 is a schematic diagram showing the invention as applied to the processing of soyabean meal.
Figure 4:
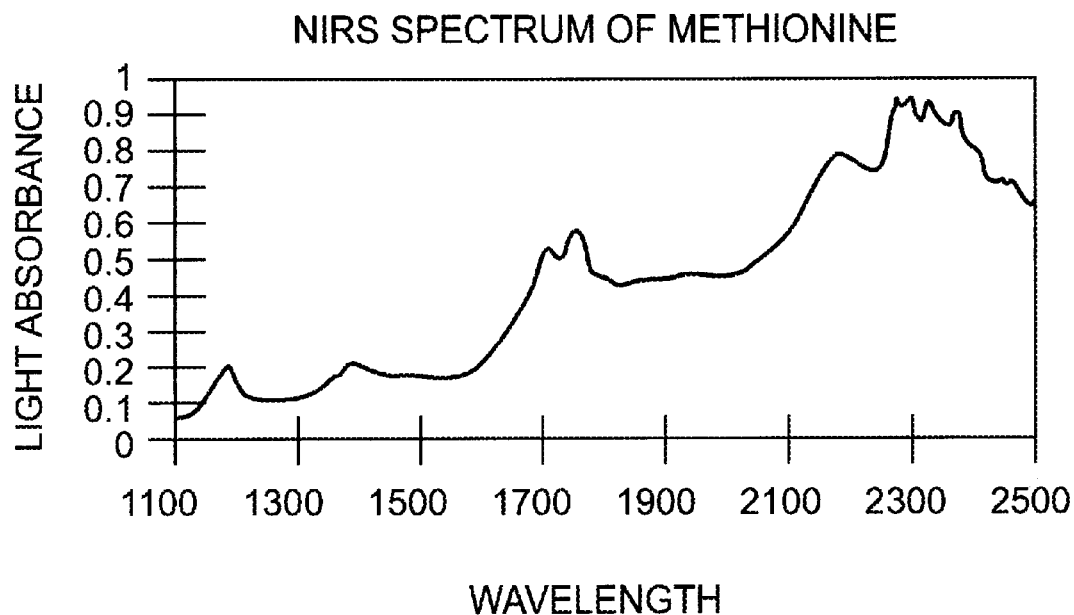
FIG. 4 illustrates an NIR spectrum of methionine.
Figure 5:
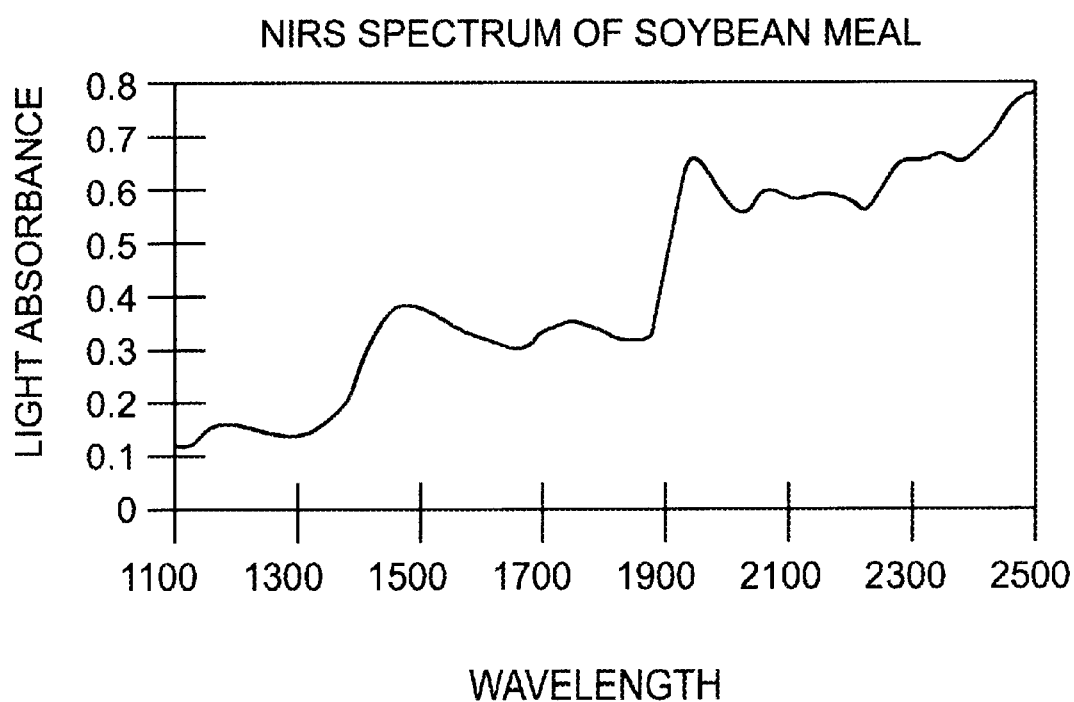
FIG. 5 illustrates an NIR spectrum of soyabean meal.

FIG. 3 illustrates schematically the application of the system in the production of an enhanced soyabean meal. Batches of soyabean meal 210 are sampled by a sampler 215 and subjected to near infrared reflectance spectroscopy by spectrometer 217. The spectrum is compared at 219 to spectra stored in a database 221 relating the spectra to the amino acid content. FIG. 4 illustrates the NIRS spectrum of methionine and FIG. 5 illustrates the NIRS spectrum of soyabean meal. By comparing FIGS. 4 and 5, it will be seen that a direct quantification of the soyabean meal composition is not possible because the spectrum of soyabean meal lacks distinguishable peaks, and the spectrum of FIG. 5 is actually a composite spectrum of different substances present in the soyabean meal. Therefore, another way of assessing the amino acid content from the spectrum is to establish the database 221 relating spectra to amino acid content measured by other analysis techniques. The result of the comparison at 219 is, therefore, a nutrient (amino acid) profile 223. This is compared at 225 to the desired profile established by considering the ideal diet for the animal. The batch is then accepted or rejected at step 227 and, if accepted, a nutrient, in this case amino acid additive is added at step 229 to achieve the desired nutrient profile in the feedstuff.

Figure 6:
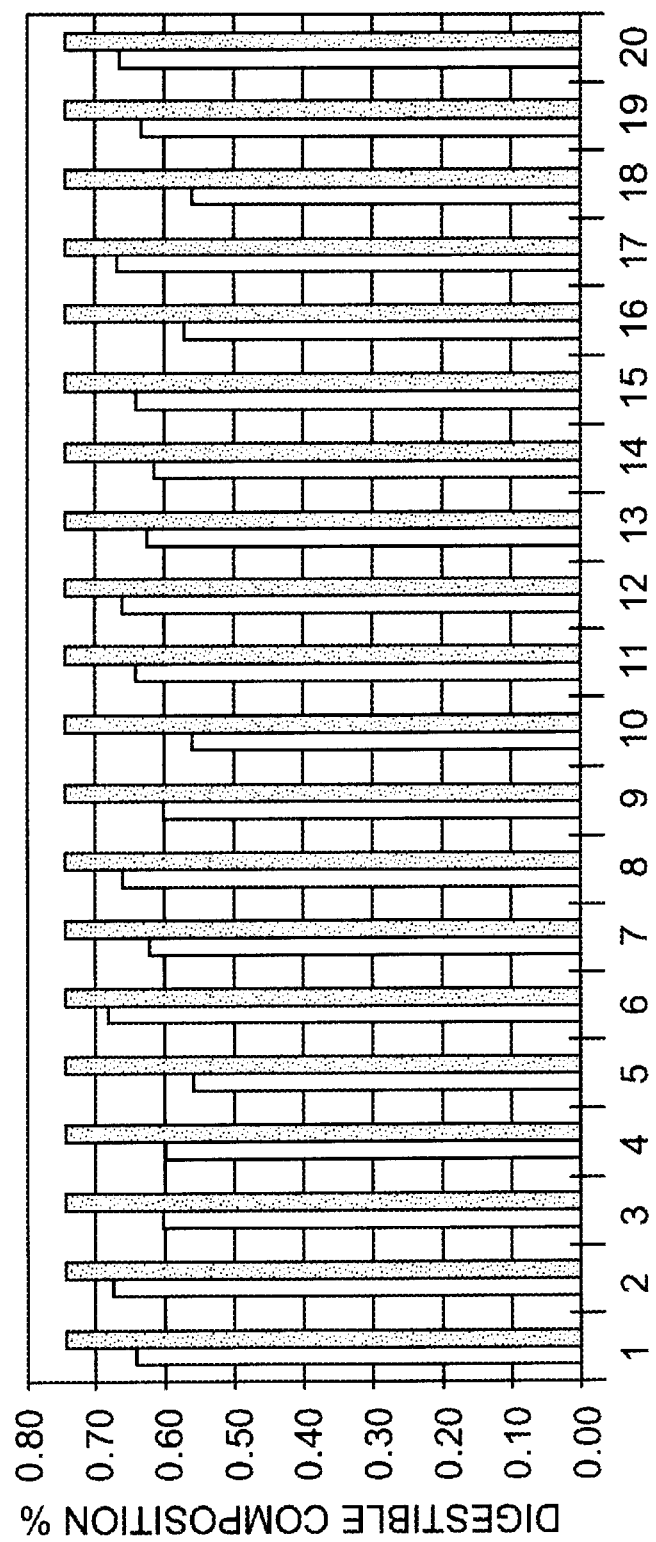
FIG. 6 illustrates the digestible methionine content of natural soyabean meal and an animal feed product containing the enhanced soyabean meal.

FIG. 6 illustrates the level of digestible methionine in the incoming soyabean meal, which can be seen to vary markedly, and the level in the complete feed, i.e. after enhancement by the addition of synthetic methionine. It can be seen that a guaranteed level of 0.74% can be achieved, compared to the 0.62% average in the raw product.

The embodiment thus described allows the selecting and enhancing of feedstuffs for use in an animal feed product by analyzing the statistical distribution of the nutritional content of batches of the feedstuff and calculating the number of batches within a predetermined range of a desirable nutrient composition. The cost of enhancing the feedstuff by adding nutrient additives is calculated and batches of the feedstuff are accepted or rejected, with the enhancement step only applied to the accepted batches.

It will be understood that a product of this process is of value in that it has a desired nutritional profile, with lower than natural variance, while being available in sufficient amounts and value that is acceptable to feedstuff users. In the particular example of soyabean meal explained above, there is additional advantage in that the product has a low protein content, yet high amino acid content. The low protein content is effective in reducing the environmental pollution produced by animals consuming the final feed product. The invention makes it possible to produce such a product by selecting the raw material with reference to the nutritional content so avoiding systematic overformulation. Further, statistical analysis of the frequency distribution of the nutritional content amongst batches of the feedstuff allows the optimisation of the selection of the raw material having regard to the amount of product to be produced, its cost of production, and the desired nutritional profile.

We claim:

1. A method comprising the steps of:
   analyzing the nutritional composition of batches of a raw material for use in an animal feed product;
   comparing the nutritional composition with a predetermined nutritional composition;
   calculating the amount of supplemental nutrient needed to bring the composition of the batch to the predetermined-nutritional composition;
   determining a cluster of batches of raw material for which the amount of supplemental nutrient needed is similar within that cluster;
   determining a threshold supplemental nutrient amount that would be economically and nutritionally favorable for addition to the batches of raw material within the cluster;
   screening the batches to reject those for which the amount of supplemental nutrient needed is greater than the threshold supplemental nutrient amount and to accept those for which the amount of supplemental nutrient needed is no more than the threshold supplemental nutrient amount; and
   supplementing only the accepted batches of raw material with the calculated amount of supplemental nutrient.

2. A method according to claim 1, further comprising the step of analyzing the statistical distribution of the nutritional content of the batches of the raw material; assessing on the basis of the statistical distribution the number of batches for which the amount of supplemental nutrient needed is less than the threshold supplemental nutrient amount; and on condition that said number of batches is greater than a predetermined value, performing said screening and supplementing steps.

3. A method according to claim 2, further comprising setting, with respect to said threshold supplemental nutrient amount and said statistical distribution, a nutritional composition threshold and wherein the step of screening comprises comparing the nutritional content of each batch with said nutritional composition threshold and rejecting those batches falling below said nutritional composition threshold.

4. A method according to claim 3, wherein the nutritional composition threshold defines a boundary of a range of nutritional compositions compared to a predefined nutritional composition profile and said step of analyzing the statistical distribution of the nutritional content of batches of the raw material comprises estimating the percentage of batches that are clustered within said range.

5. A method according to claim 1, wherein the step of analyzing the nutritional composition comprises measuring the amount of at least one amino acid in the raw material.

6. A method according to claim 1, wherein the step of analyzing the nutritional composition comprises measuring the digestibility of the nutrient in the raw material.

7. A method according to claim 5, wherein said amino acid is at least one of methionine and lysine.

8. A method according to claim 1, wherein the step of analyzing the nutritional composition comprises measuring the amount of at least one amino acid in the raw material by near infrared reflectance spectroscopy.

9. A method according to claim 1, wherein the step of analyzing the nutritional composition comprises measuring the amount of fat in the raw material.

10. A method according to claim 1, wherein the raw material is soyabean meal.

11. A method according to claim 1, wherein the raw material is corn.

12. A computer program comprising program code means for controlling and executing the method of claim 1.

13. A computer readable storage medium encoding the computer program of claim 12.

14. A nutritionally supplemented raw material for use in the manufacture of an animal feed product produced by the method according to claim 1.

15. A method according to claim 1, which further comprises determining if an economically favorable quantity of raw material exists of the clusters for which supplemental nutrient needed is below or at the threshold supplemental nutrient amount; and on condition that an economically favorable quantity of raw material exists, performing the screening and supplementing steps.

* * * * *

UNITED STATES PATENT AND TRADEMARK OFFICE
CERTIFICATE OF CORRECTION

PATENT NO.     : 6,532,420 B1
DATED          : March 11, 2003
INVENTOR(S)    : Haeffner et al.

It is certified that error appears in the above-identified patent and that said Letters Patent is hereby corrected as shown below:

<u>Title page, Item [54] and Column 1, line 1,</u>
Delete the title in its entirety and insert therefor
-- IMPROVEMENTS IN OR RELATING TO THE PRODUCTION OF ANIMAL FEED --.
Item [75], Inventors, "Saint-Could (FR)" should read -- Saint-Cloud (FR) --.

<u>Column 7,</u>
Line 45, "predetermined-nutritional" should read -- predetermined nutritional --.

Signed and Sealed this

Twenty-second Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,532,420 B1
DATED : March 11, 2003
INVENTOR(S) : Jurgen Erwin Friedrich Haeffner et al.

It is certified that error appears in the above-identified patent and that said Letters Patent is hereby corrected as shown below:

<u>Title page,</u>
Item [*] Notice, "Subject to any disclaimer, the term of this patent is extended or adjusted under 35 U.S.C. 154(b) by 0 days" should read -- Subject to any disclaimer, the term of this patent is extended or adjusted under 35 U.S.C. 154(b) by 32 days --.

Signed and Sealed this

Fifteenth Day of November, 2005

JON W. DUDAS
*Director of the United States Patent and Trademark Office*